United States Patent [19]

Welch

[11] Patent Number: 5,050,991

[45] Date of Patent: Sep. 24, 1991

[54] HIGH OPTICAL DENSITY MEASURING SPECTROMETER

[75] Inventor: Jeanne A. Welch, Laurel, Md.

[73] Assignee: The United States of America as represented by the Secretary of the Navy, Washington, D.C.

[21] Appl. No.: 415,740

[22] Filed: Sep. 29, 1989

[51] Int. Cl.$^5$ .............................................. G01J 3/36
[52] U.S. Cl. .................................... 356/326; 356/328
[58] Field of Search ............... 356/326, 328, 436, 437; 250/373

[56] References Cited

U.S. PATENT DOCUMENTS

| 4,084,906 | 4/1978 | Bibbero | 356/418 |
| 4,375,919 | 3/1983 | Busch | 356/326 |
| 4,448,529 | 5/1984 | Krause | 356/310 |
| 4,755,056 | 7/1988 | Yasuda et al. | 250/373 X |
| 4,870,275 | 9/1989 | Ozdemir | 356/301 X |

FOREIGN PATENT DOCUMENTS 54-13359 1/1979 Japan .................................. 356/328

OTHER PUBLICATIONS

Birch et al., "Multiplexed Array Fluorometer", J. Phys. E: Sci. Instrum. 21 (1988), pp. 415-417.
Raman Lasers (Review), A. Z. Grasyuk, Sov. J. Quant. Electron, vol. 4, No.3, Sep. 1974.

Primary Examiner—Vincent P. McGraw
Attorney, Agent, or Firm—Thomas E. McDonnell; George Jameson

[57] ABSTRACT

An apparatus is disclosed for measuring the spectra of a high optical density sample having substantially known optical properties. In a preferred embodiment, the apparatus comprises: a laser for producing a light beam; a Raman cell responsive to the light beam for generating a first light containing a plurality of preselected wavelength components; an optical system for directing the first light through the sample; a dispersion device for spatially separating the first light passed through the sample into its plurality of preselected wavelength components; a plurality of light detectors positioned to respectively receive the spatially-separated preselected wavelength components and to convert the photons in each of the spatially-separated preselected components into a plurality of associated photocurrents having amplitudes respectively representative of the numbers of photons in the spatially-separated preselected wavelength components; and a photon counter for respectively converting the plurality of associated photocurrents into a plurality of photon counts corresponding to the transmittance of the sample at the respective preselected wavelength components of the first light passing through the sample. In a modification of the invention, the apparatus further includes an energy meter adapted to receive a portion of the light beam for generating an energy signal representative of the total energy in the light beam, and processing means responsive to the plurality of photon counts and to the energy signal for determining the output transmittance of the sample at the preselected wavelength components of the first light passing through the sample.

17 Claims, 1 Drawing Sheet

HIGH OPTICAL DENSITY MEASURING SPECTROMETER

BACKGROUND OF THE INVENTION

1. Field of the Invention

The present invention relates to spectrometers and particularly to an apparatus for measuring the spectra of a high optical density sample having substantially known optical characteristics.

2. Description of the Prior Art

Optical spectrometers measure the fraction of energy absorbed or attenuated by a sample of material from a beam of optical radiation as a function of the frequency of the radiation. These optical spectrometers are based on a dispersive element, which may be a prism or a diffraction grating, such as a plane or concave diffraction grating. The dispersive element selectively disperses the attenuated radiation from the sample into various spectral components of different wavelengths which, in turn, are focused upon some sort of detection means. The detection means transduces these incident spectral components into some usable form.

Various types of detectors may be used such as, for example, film, photodiode circuits or a multielement detection system. In multielement or parallel detection, the attenuated source radiation from the sample is dispersed rather than wavelength scanned, and the entire spectrum is collected simultaneously by an array of detectors. The simplest such parallel-detection system is the photographic emulsion. Optoelectronic image detectors, such as self-scanned photodiode arrays and multichannel plates, are other examples of parallel detectors. The optoelectronic detector is too subject to blooming (channel-to-channel cross-talk due to overspill of photon-generated charge) and spectral interference (where neighboring features are masked) to be employed in low transmittance applications. Blooming and spectral interference are minimized with a two-dimensional optoelectronic image detector but not sufficiently enough for high optical density applications. In a proposed direct-reader, a nonscanned photomultiplier array is used for detection. However, broadband radiation, instead of discrete radiation, is used for the source. The detection limits and resolution required in high optical density spectroscopy are not attainable in a direct-reader.

It should also be noted that the typical prior art spectrometer utilizes a lamp, such as an Xenon lamp, for a radiation source. Such a lamp produces optical radiation throughout the entire spectrum. Thus, the optical power from the lamp is spread across the entire spectrum. As a result, the typical prior art spectrometer substantially cannot detect any light passing through a sample which has an optical density greater than 6. In other words, the typical prior art spectrometer can only reliably detect light from a sample that only attenuates the light incident on the sample by no more than 6 orders of magnitude.

Various prior art spectrometers employing a standard scanning spectrometer optical design with increased baffling have been implemented, but optical density limits of only 12 have been achieved.

One prior art scanning spectrometer, that enjoyed a minor amount of success, used low-resolution radiation generated by an Xenon lamp and filtered through a double monochromator to illuminate the high density sample. The attenuated radiation from the sample was collected with a GaAs detector using photon-counting techniques. This technique allowed a broad, low-resolution spectrum of the sample to be determined.

Another prior art scanning spectrometer used a high-resolution, tuned, doubled, flashlamp-pumped-dye laser as the radiation source with the appropriate substitution of pulsed-detection techniques. This technique is not satisfactory for a number of reasons, namely, the system contains a number of moving parts that must constantly be aligned (including the optics required to cover the broad spectral range of the laser tuning), the calibration is difficult and unreliable, and the dynamic range of the system is limited to only 9 orders of magnitude.

OBJECTS OF THE INVENTION

Accordingly, it is an object of this invention to provide a novel spectrometer.

Another object of this invention is to provide an apparatus for measuring the spectra of a high optical density sample having substantially known optical properties.

A further object of this invention is to provide an apparatus for measuring the spectra of a sample having substantially known optical properties and having an optical density greater than 12.

SUMMARY OF THE INVENTION

These and other objects of this invention are achieved by providing an apparatus for measuring the spectra of a high optical density sample having substantially known optical properties. The apparatus includes: first means for producing a light beam; second means responsive to said light beam for producing a first light containing a plurality of preselected wavelength components; means for optically directing said first light through said sample; dispersion means for spatially separating said first light passed through said sample into its plurality of preselected wavelength components; a plurality of light detectors positioned to respectively convert photons in each of said spatially-separated preselected wavelength components into a plurality of associated photocurrents having amplitudes respectively representative of the numbers of photons in said spatially-separated preselected wavelength components; and means for respectively converting said plurality of associated photocurrents into a plurality of photon counts corresponding to the transmittance of said sample at the respective said preselected wavelength components of said light passing through said sample. In a modification of the invention, the apparatus further includes: means coupled to said producing means and being responsive to a calibrated portion of said light beam for generating an energy signal representative of the total energy in said light beam; and processing means responsive to said plurality of photon counts and to said energy signal for determining the output transmittance of said sample at the 12 respective said preselected wavelength components of said first light passing through said sample.

BRIEF DESCRIPTION OF THE DRAWING

These and other objects, features and advantages of the invention, as well as the invention itself, will become better understood by reference to the following detailed description when considered in connection with the accompanying drawing wherein:

The FIGURE illustrates a schematic block diagram of a preferred embodiment of the invention.

DETAILED DESCRIPTION OF THE PREFERRED EMBODIMENT

Figure 1:
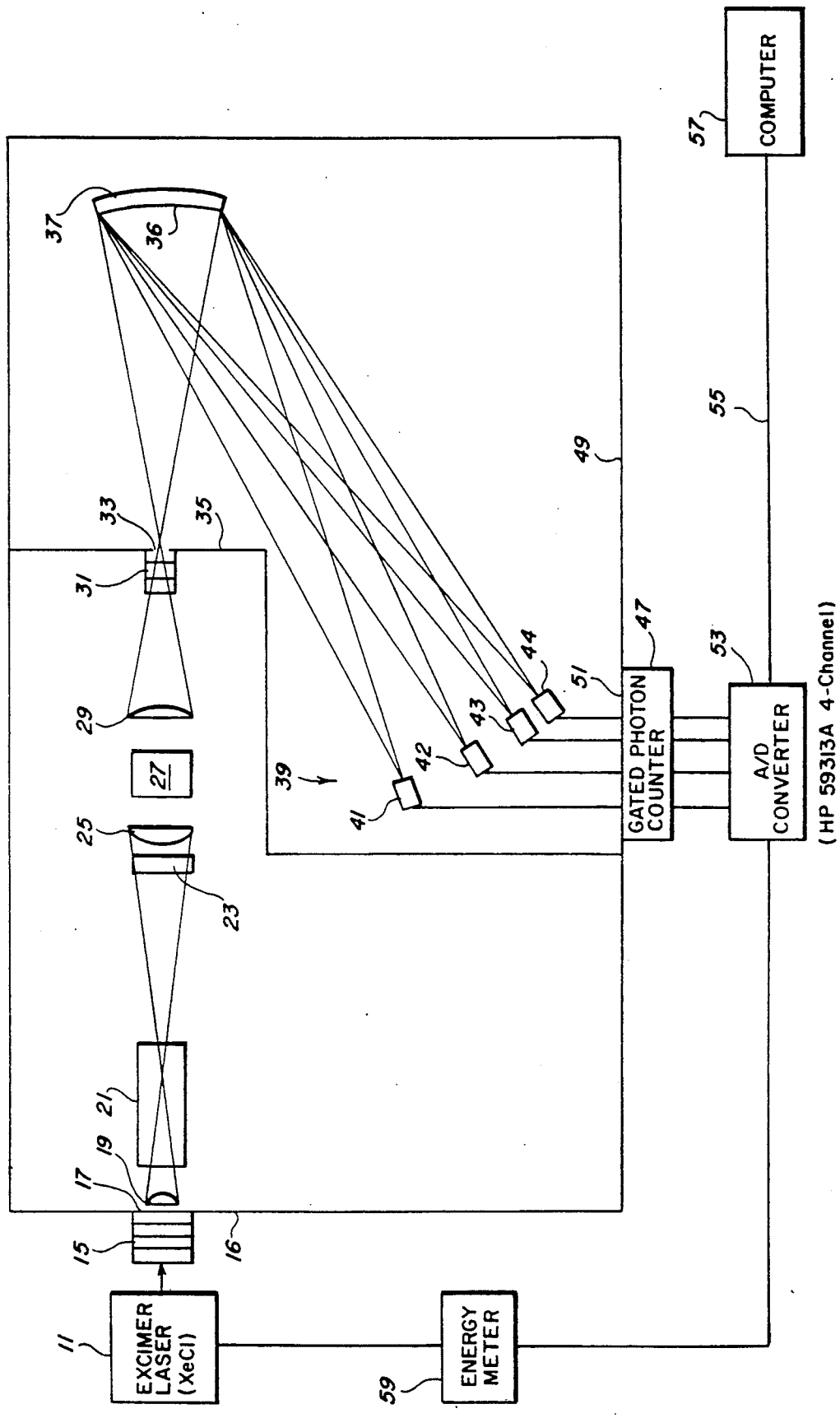

Referring now to the FIGURE, a schematic block diagram of a preferred embodiment of the invention is shown. An exemplary high-power excimer laser 11 is used to develop a high power, narrow linewidth, light beam or laser radiation. For purposes of this description, the exemplary laser 11 is designed to operate with Xenon chloride (XeCl) gas and, hence, operates at 308 nm. However it should be understood that any high power laser or laser array could be utilized to produce a high power laser radiation at a desired wavelength.

The high power light beam from the laser 11 enters a shielded enclosure 13 through a light baffle 15, which is mounted to an external side 16 of the enclosure 13 to cover an entrance 17 into the enclosure 13. The shielded enclosure 13 provides protection from the electrical noise generated by the laser 11 and from any ambient or scattered light in the area around the enclosure 13. The light baffle 15 provides increased protection against any scattered and ambient light along the direct path of the high power laser light beam at the entrance 17 to the shielded enclosure 13. This light beam passes through the light baffle 15, through the entrance 17, and into a lens 19 which focuses the light beam into a small spot in a Raman cell 21. The Raman cell 21 shifts the wavelength of the incident light beam into one or more component wavelengths on both sides of the wavelength of the laser 11.

It should be noted that the Raman cell 21 can be designed to produce the component wavelengths that are needed for a desired particular application. More particularly, the number and frequency of the wavelength shifts of the Raman cell 21 are controlled by the medium of the Raman cell 21, the wavelength of the laser 11, and the physical operating conditions (i.e., pressure, temperature, etc.). The medium of a Raman cell can be comprised of one or more gases, one or more liquids mixed together, or a solid comprised of one or more materials. In addition, two or more Raman cells can be cascaded, with each Raman cell having a different medium. For a more complete explanation of Raman cells and the generation of a plurality of intense component wavelengths by the efficient wavelength conversion of an excimer laser with stimulated Raman scattering, refer to the published article of A. Z. Grasyuk, "Raman Lasers", Sov. J. Quant. Elect., Vol. 4, No. 3, pages 269-282 (September, 1984).

For purposes of this description, assume that the Raman cell 21 produces a plurality of component wavelengths, but only 4 of these component wavelengths are desired for a given application.

After the Raman conversion of the wavelength of the laser light beam into a plurality of component wavelengths in the laser light beam, the beam exits from the Raman cell. Any extraneous Raman radiation or light outside of the exemplary 4 desired component wavelengths is blocked by a blocking filter 23, while the 4 desired or preselected component wavelengths pass through the blocking filter 23 to a lens 25.

Lenses 19 and 25 collectively comprise a telescope, with lens 19 focusing the light beam from the laser 11 into a small spot in the Raman cell 21 and lens 25 collimating the light beam from the Raman cell 21 to pass through a high optical density sample 27. The sample 27 can have an optical density of greater than −12. As a result, the light beam is attenuated by the sample 27.

It should be noted at this time that the apparatus of the FIGURE is implemented to verify what the transmittance of the sample 27 is to various preselected component wavelengths desired for a particular application. The apparatus of the FIGURE can be used on a production line to verify that the sample 27 has the desired optical qualities. Basically, the apparatus of the FIGURE is a quality assurance apparatus. It can be used, for example, to verify that a filter or filter sample is filtering out undesired wavelengths. If, in another application paint is being manufactured, a diluted liquid paint sample can be checked to see if the composition of a batch of the paint conforms to the desired specifications by passing the associated component wavelengths therethrough.

Thus, the application determines the sample and the sample, in turn, determines what particular component wavelengths are desired to verify the transmittance of the sample 27 to those wavelengths. In any event, some prior knowledge of the composition or optical properties of the sample 27 is needed to verify that the sample 27 is substantially what it is supposed to be.

Once the desired component wavelengths for the sample 27 are determined, the Raman cell 21 must be implemented to have the proper medium to generate those wavelengths of light. And the laser 11 must produce enough light so that some portion of the desired component wavelengths of light can pass through the high optical density sample 27 for subsequent detection (to be discussed). In some cases the transmittance of the light beam passing through the sample 27 will be attenuated by 12 to 15 orders of magnitude.

The resultant attenuated light beam from the sample 27 is focused by a lens 29 through a light baffle 31 and a slit 33 in a light shielded enclosure 35 to pass into the enclosure 35. The light shielded enclosure 35 is disposed within the shielded enclosure 13 to provide additional shielding from scattered light.

The light passing through the slit 33 provides the desired spectral resolution and expands to fill or cover the front surface 36 of a high-resolution, long-focal-length concave holographic 17 diffraction grating 37. The concave diffraction grating is a non-scanning dispersive element which spatially separates the attenuated light beam from the sample 27 into its exemplary 4 component wavelengths and focuses those spatially-separated component wavelengths of light into an array 39 of photomultiplier detectors 41-44 positioned to respectively receive the component wavelengths of light.

The detectors 41-44 respectively convert the photons in each of the spatially-separated component wavelengths of light into a plurality of associated photocurrents having amplitudes representative of the numbers of photons in the respective spatially-separated preselected component wavelengths of light. This plurality of photocurrents is respectively applied to a plurality of associated channels (not shown) in a gated photon counter 47, which is mounted to an external side 49 of the light shielded enclosure 35 (but within the enclosure 13) and covers an opening 51 in the side 49. The photon counter 47 may be implemented by means of a Stanford Research gated photon counter having part number SR 400. Each channel in the photon counter 49 counts the electrons in the associated photocurrent applied thereto to develop an electron count which corresponds to the photon count or number of photons in the particular component wavelength of light that was incident on its associated one of the detectors 41–44. Thus the photon counter 49 essentially converts the plurality of photocurrents from the detectors 41–44 into a plurality of photon counts corresponding to the transmittance of the sample 27 at the respective preselected component wavelengths of light passed through the sample 27.

Additional circuit components may be added to the above-discussed structural components in the FIGURE to determine the absolute transmittance of the sample to the preselected component wavelengths of light, as discussed below.

The four electron counts, or signals, from the photon counter 47 are converted from analog signals to digital signals by a four-channel, analog-to-digital converter 53. The analog-to-digital converter 53 may be implemented by means of a Hewlett-Packard analog-to digital converter having part number HP 59313A. The four digital signals from the converter 53 are applied in parallel by way of a composite line 55 to a digital computer or processor 57 for data and signal processing. The data from the converter 53 is collected by the computer 57 over a long time and averaged to obtain the final absolute transmittance of the sample 27 to the preselected component wavelengths of light.

An energy meter 59 is coupled to the laser 11 for generating an energy signal representative of the total laser energy developed by the laser 11. This energy signal is initially developed be the energy meter 59, converted into a digital signal by the converter 53, and applied to the computer 57 and stored therein. The apparatus of the FIGURE is also initially calibrated by removing the sample 27, allowing the laser radiation to pass through the spectrometer in the absence of sample attenation, and computing what fraction of the total energy outputted by the laser 11 passes through the spectrometer of the FIGURE when the sample 27 is removed. This calibration signal is also stored in the computer 57. As a result, the calibration signal, the total energy signal from the energy meter 59, and the digitized photon counts derived from the photon counter 47 (and representative of the amounts of light in the preselected component wavelengths that pass through the sample 27) are readily utilized by the computer 57 to compute the output transmittance of the sample 27 to the preselected component wavelengths that pass through the sample 27.

Therefore, what has been described is an apparatus for measuring the spectra of high optical density samples having optical densities greater than 12. In the apparatus, a manifold of intense laser lines is generated by the efficient wavelength conversion of an excimer laser output with stimulated Raman scattering. The multiline Raman beam is attenuated by the sample, and then spatially dispersed to its component lines. Each Raman line is individually detected by means of a multi-element, non-scanning detector system.

It should therefore readily be understood that many modifications and variations of the present invention are possible within the purview of the claimed invention. It is therefore to be understood that, within the scope of the appended claims, the invention may be practiced otherwise than as specifically described.

What is claimed and desired to be secured by Letters Patent of the United States is:

1. An apparatus for measuring the spectra of a high optical density sample having substantially known optical properties, said apparatus comprising:
    means for generating light containing a plurality of preselected wavelength components;
    means for optically directing said light through said sample;
    dispersion means for spatially separating said light passed through said sample into its plurality of preselected wavelength components;
    a plurality of light detectors positioned to respectively convert photons in each of said spatially-separated preselected wavelength components into a plurality of associated photocurrents having amplitudes respectively representative of the numbers of photons in said spatially-separated preselected wavelength components; and
    means for respectively converting said plurality of associated photocurrents into a plurality of photon counts corresponding to the transmittance of said sample at the respective said preselected wavelength components of said light passing through said sample.

2. The apparatus of claim 1, wherein said generating means comprises first means for producing a light beam and second means responsive to said light beam for producing said light containing said plurality of preselected component wavelengths prior to directing said light through said sample.

3. The apparatus of claim 2, wherein said first means is a laser and said second means is a Raman cell.

4. The apparatus of claim 1, wherein said plurality of light detectors comprises a plurality of photomultiplier detectors for receiving the respective preselected wavelength components of said light and wherein said converting means comprises a photon counter.

5. An apparatus for measuring the spectra of a high optical density sample having substantially known optical properties, said apparatus comprising:
    means for developing a first light containing a plurality of preselected component wavelengths, said developing means comprising first means for producing a light beam and second means responsive to said light beam for producing said first light containing said plurality of preselected component wavelengths;
    optical means for directing said first light through said sample, said first light being attenuated by said sample, said optical means comprising a first lens for focusing said light beam from said first means into said second means and a second lens for collimating said first light to pass through said sample;
    dispersion means responsive to said attenuated first light for spatially separating said attenuated first light into its preselected component wavelengths and respectively focusing said spatially-separated preselected component wavelengths at associated ones of a plurality of focal points at a plurality of positions respectively determined by the focal length of said dispersion means and by the respective wavelengths of said spatially-separated preselected component wavelengths, said optical means further comprising a third lens for causing said attenuated first light to expand to cover said dispersion means;
    a plurality of detection means respectively positioned at said plurality of focal points for selectively converting the photons in said spatially-separated preselected component wavelengths of said attenuated first light into a plurality of associated photocurrents having amplitudes respectively representative of the numbers of photons in each of said spatially-separated preselected component wavelengths; and means for respectively converting said plurality of associated photocurrents into a plurality of photon counts corresponding to the transmittance of said sample at the respective said preselected component wavelengths of said first light passing through said sample.

6. The apparatus of claim 5 wherein:
said first means is a laser; and
said second means is a Raman cell.

7. The apparatus of claim 5 further including:
a filter disposed between said second means and said second lens for blocking extraneous light outside of said plurality of preselected component wavelengths.

8. The apparatus of claim 5 wherein:
said dispersion means is a diffraction grating.

9. The apparatus of claim 5 wherein:
said plurality of detection means is comprised of a plurality of photomultiplier detectors respectively positioned at said plurality of focal points to receive the respective preselected component wavelengths of said attenuated first light.

10. The apparatus of claim 5 wherein:
said converting means is a photon counter.

11. The apparatus of claim 5 further including:
means coupled to said first means and being responsive to a portion of said light beam for generating an energy signal representative of the total energy in said light beam; and
processing means responsive to said plurality of photon counts and to said energy signal for determining the output transmittance of said sample at the respective said preselected component wavelengths of said first light passing through said sample.

12. The apparatus of claim 11 wherein:
said generating means is an energy meter; and
said processing means is comprised of an analog-to-digital converter for selectively converting said energy signal and said plurality of photon counts to a plurality of digital signals, and computing means responsive to said plurality of digital signals for determining the output transmittance of said sample at the respective said preselected component wavelengths of said first light passing through said sample.

13. An apparatus for measuring the spectra of a high optical density sample having substantially known optical properties, said apparatus comprising:
means for developing a first light containing a plurality of preselected component wavelengths comprising a laser means for producing a light beam, and a Raman cell means responsive to said light beam for producing said first light;
optical means for directing said first light through said sample, said first light being attenuated by said sample;
dispersion means responsive to said attenuated first light for spatially separating said attenuated first light into its preselected component wavelengths and respectively focusing said spatially-separated preselected component wavelengths at associated ones of a plurality of focal points at a plurality of positions respectively determined by the focal length of said dispersion means and by the respective wavelengths of said spatially-separated preselected component wavelengths, said dispersion means comprising a diffraction grating, said optical means further including a first lens for focusing said light beam from said laser means into said Raman cell means, a second lens for collimating said first light to pass through said sample, and a third lens for causing said attenuated first light to expand to cover said diffraction grating;
a plurality of detection means respectively positioned at said plurality of focal points for selectively converting the photons in said spatially-separated preselected component wavelengths of said attenuated first light into a plurality of associated photocurrents having amplitudes respectively representative of the number of photons in each of said spatially-separated preselected component wavelengths; and
means for respectively converting said plurality of associated photocurrents into a plurality of photon counts corresponding to the transmittance of said sample at the respective said preselected component wavelengths of said first light passing through said sample, said converting means comprising a photon counter.

14. An apparatus for measuring the spectra of a high optical density sample having substantially known optical properties, said apparatus comprising:
means for producing a light beam;
means responsive to said light beam for generating a first light containing a plurality of preselected component wavelengths;
optical means for directing said first light through said sample, said first light being attenuated by said sample;
dispersion means responsive to said attenuated first light from said sample for spatially separating said attenuated first light into its preselected component wavelengths and focusing each of said spatially-separated selected component wavelengths of said attenuated first light into an associated focal point at an associated position determined by said each component wavelength and by the focal length of said dispersion means;
a plurality of detection means respectively positioned at said plurality of focal points for converting the photons in each of said preselected component wavelengths of said attenuated first light into associated photocurrents having amplitudes representative of the numbers of photons in respective ones of said preselected component wavelengths of said attenuated first light;
means for respectively converting said associated photocurrents into a plurality of photon counts respectively corresponding to the numbers of photons in said preselected component wavelengths of said attenuated first light;
means coupled to said producing means and being responsive to a portion of said light beam for developing an energy signal representative of the total energy in said light beam; and
processing means responsive to said plurality of photon counts and to said energy signal for determining the output transmittance of light passing through said sample said optical means including a first lens for focusing said light beam from said producing means into said generating means, a second lens for collimating said first light to pass through said sample, and a third lens for causing said attenuated first light to expand to cover said dispersion means.

15. The apparatus of claim 14 further including:

a first enclosure containing said dispersion means and said plurality of detection means for shielding said dispersion means and said plurality of detection means from extraneous light, said first enclosure including a first opening to mount said converting means thereto without allowing extraneous light to enter said first enclosure, and a slit;

a second enclosure containing said optical means, said generating means, said sample, said first enclosure, a first light baffle mounted to said first enclosure and covering said slit to enable only said attenuated first light from said sample to pass therethrough to said dispersion means and a second opening; and a second light baffle externally mounted to said second enclosure and covering said second opening to substantially enable only said light beam from said producing means to pass into said optical means.

16. The apparatus of claim 15 wherein said optical means includes:

a first lens disposed between said second light baffle and said generating means for focusing said light beam being passed through said second light baffle into said generating means;

a second lens disposed between said generating means and said sample for collimating said first light and directing said collimated first light through said sample; and a third lens disposed between said sample and said first light baffle for focusing said attenuated first light into said first light baffle and through said slit, said light from said slit expanding to cover said dispersion means.

17. The apparatus of claim 16 wherein:

said producing means is a laser;

said generating means is a Raman cell;

said dispersion means is a diffraction grating;

said converting means is a photon counter;

said developing means is an energy meter; and said processing means is comprised of an analog-to-digital converter for selectively converting said energy signal and said plurality of photon counts to a plurality of digital signals, and computing means responsive to said plurality of digital signals for determining the output transmittance of said sample at the respective said preselected component wavelengths of said first light passing through said sample.

* * * * *